(12) United States Patent
Rhodes

(10) Patent No.: US 6,284,797 B1
(45) Date of Patent: Sep. 4, 2001

(54) TOPICAL TREATMENT OF PAIN AND TO PROMOTE HEALING

(76) Inventor: Donald A. Rhodes, 4833 S. Staples, Corpus Christi, TX (US) 78411

( * ) Notice: Subject to any disclaimer, the term of this patent is extended or adjusted under 35 U.S.C. 154(b) by 0 days.

(21) Appl. No.: 09/289,878

(22) Filed: Apr. 12, 1999

(51) Int. Cl.⁷ .......................... A01N 43/00; A01N 33/02; A61K 31/33
(52) U.S. Cl. .......................... 514/627; 514/183; 514/450; 514/212.01; 514/634; 514/656
(58) Field of Search ........................................ 514/627, 183, 514/450, 634, 212.01, 656; 424/401, 448

(56) References Cited

U.S. PATENT DOCUMENTS

| 4,997,853 | * | 3/1991 | Bernstein . | |
| 5,063,060 | * | 11/1991 | Bernstein . | |
| 5,134,166 | * | 7/1992 | Bernstein | 514/627 |
| 5,178,879 | * | 1/1993 | Adekunle . | |
| 5,296,225 | * | 3/1994 | Adekunle . | |
| 5,665,378 | * | 9/1997 | Davis . | |
| 6,103,266 | * | 8/2000 | Tapolsky et al. | 424/484 |

* cited by examiner

Primary Examiner—Thurman K. Page
Assistant Examiner—S. Howard
(74) Attorney, Agent, or Firm—G Turner Moller

(57) ABSTRACT

A topical therapeutic preparation includes capsaicin which is an extract of peppers or chiles and which is a potent local pain killer. The ointment also includes a norepinephrine inhibitor and preferably a vasodilator which act to promote blood circulation in the treatment area and thereby promote healing of tissues in the treatment area. The ointment also preferably includes a local pain killer to offset the irritating effects of the capsaicin and a promoter of transcutaneous absorption.

19 Claims, No Drawings

TOPICAL TREATMENT OF PAIN AND TO PROMOTE HEALING

This invention comprises a topical preparation used to reduce pain and promote healing of the skin and tissues adjacent the skin.

BACKGROUND OF THE INVENTION

Capsaicin creams, ointments, gels or lotions are well known in the art. Capsaicin is the pungent extract of peppers or chiles and, chemically, is trans-8-methyl-N-vanillyl-6-nonenamide. Capsaicin is believed to act on a subset of primary afferent nerves mostly of the c-fiber type. It binds to a receptor site at the nerve ending and therefore interferes with the binding of substance P. There are believed to be two phases of action, first excitation and then desensitization of the nerve to nociceptive impulses. The excitation results in the shot of hot peppers or a burning/tingling sensation when applied to the skin. The desensitization results from depletion of substance P and interference with afferent transmission in a nontetrodotoxin dependent manner. Clinically, the overall effect is pain relief.

Capsaicin can be readily obtained by the ethanol extraction of the fruit of capsicum frutescens or capsicum annum. It is available commercially from a variety of suppliers and can also be prepared synthetically by published methods. In some commercially available forms of capsaicin, a slightly different composition known as pseudocapsaicin is present. This pseudocapsaicin is pharmacologically indistinguishable from natural capsaicin. The present invention encompasses the use of both forms, and where the term capsaicin is used, both forms are meant.

Disclosures of capsaicin creams, ointments and gels and their operating mechanisms are disclosed in U.S. Pat. Nos. 4,997,853; 5,063,060; 5,178,879; 5,296,225 and 5,665,378.

SUMMARY OF THE INVENTION

In this invention, a capsaicin preparation is provided which not only reduces pain but which also promotes healing of the skin and tissue adjacent the skin. This is accomplished by combining capsaicin with a norepinephrine inhibitor. Capsaicin is a known pain reliever but has no direct healing properties, i.e. any healing that occurs does so naturally without assistance by the capsaicin.

Without being bound by any particular theory, it appears that many of the successes of this invention can be explained by normalizing production and/or circulation of norepinephrine. Norepinephrine is a longer lasting version of epinephrine and assists in transmitting nerve impulses and in constricting blood vessels. Overproduction of norepinephrine causes constriction of superficial small to medium arteries and arterioles which results in trophic skin changes, demyelination of nerves and hyperesthesia. Reducing the production and/or distribution or norephinephrine results in increased superficial arterial blood flow. This increase in superficial arterial blood flow actibely assists healing those tissues adjacent the skin where the preparation is applied.

Another important component of this invention is a vasodilator. The vasodilators actively promote dilation of the blood vessels in the area where the preparation of this invention is applied. Thus, inhibition of norepinephrine in the area of treatment and the application of vasodilators both act to increase blood flow and promote healing in the treatment area.

Another important component of the preparation of this invention is a pain killer, ant-inflamminant or analgesic. Capsaicin preparations are typically irritating to the skin in the treatment area. The inclusion of a pain killer, anti-inflamminant or analgesic reduces discomfort due to the capsaicin.

A further important component of this invention is a substance that promote transcutaneous absorption. Skin has the property of preventing or reducing absorption of most materials so it is preferred in this invention to incorporate a promoter of transcutaneous absorption.

It is accordingly an object of this invention to provide an improved capsaicin preparation which reduces pain and promotes healing of tissue adjacent the skin.

Another object of this invention is to provide an improved capsaicin preparation incorporating a norepinephrine inhibitor.

A further object of this invention is to provide an improved topical preparation containing capsaicin, a norepinephrine and a vasodilator.

These and other objects and advantages of this description will become more apparent as this description proceeds, reference being made to the appended claims.

DETAILED DESCRIPTION

In this invention, a capsaicin preparation includes capsaicin,, a norepinephrine inhibitor and a therapeutically acceptable carrier. Capsaicin is employed in an effective amount, between 0.001% and 5% by weight and preferably between 0.01% and 1.0% by weight, and may be either an extract of chiles or peppers or may be synthetically manufactured.

The norepinephrine inhibitor is a psychotropic drug that interferes with release of norepinephrine, reduces the transmission or dissemination of norepinephrine or deactivates norepinephrine at the synapses. Typical norepinephrine inhibitors used in this invention are selected from a group of tricyclic antidepressants and specifically are amitriptyline, nortriptyline and doxepin. Another suitable norepinephrine inhibitor is an antipsychotic drug fluphenazine or prolixin which interferes with norepinephrine. There are a number of hypertensive medicines that reduce blood pressure by altering the effect of norepinephrine and are accordingly suitable for use in this invention. Specifically, guanidine and guanethidine alter the effects of norepinephrine and are operative in this invention.

The norepinephrine inhibitors of this invention are used in an effective amount, i.e. they are used in an amount that increases blood flow in the treatment area. In this invention, the norepinephrine inhibitors are present in 0.5–50% by weight and preferably are present on the order of about 10–20%, optimally about 15%.

The carrier may be of any suitable type and typically is selected from the group consisting of lotions, gels, ointments or creams such as are commonly used in topical preparations. A convenient manner of compounding this invention is to start with a commercially available capsaicin cream, such as CAPSAICIN TOPICAL ANALGESIC CREAM, available from Breckenridge Pharmaceutical, Inc. of Boca Raton, Fla. and add the other active ingredients. This commercial preparation has 0.025% capsaicin in a standard cream and the cream is sufficient to suspend the remaining active ingredients of this invention. The carrier is present in an effective amount, usually 1–80% by weight and also acts as a diluent.

Another important class of compounds present in preferred compositions of this invention are cardiovascular drugs that actively promote blood circulation in the treatment area by one or more mechanisms. One important group of such compounds are vasodilators that dilate small blood vessels in the treatment area. Typical vasodilators used with this invention are reserpine, nitroglycerin and hydralazine. These vasodilators are used in an effective amount, i.e. they are used in an amount that increases blood flow in the treatment area. In this invention, the vasodilators are present in 0.5–50% by weight and preferably are present on the order of about 10–20%, optimally about 15%.

Another important class of compounds present in this invention is a pain killer to offset the irritation caused by the capsaicin. The pain killer may be an anti-inflamminant and/or analgesic such as hydrocortisone cream, a non-steroidal anti-inflamminant such as ibuprofen, aspirin or other salicylates, or other pain killers such as diflunisal, fenoprofen, indomethacin, meclofenamate, naproxen, oxyphenbutazone, phenylbutazone, piroxicam, sulindac, tolmetin, zomepirac, idocaine, benzocaine, or lidocaine.

The pain killers of this invention are used in an effective amount, i.e. they are used in an amount that substantially reduces the topical irritation caused by the capsaicin. In this invention, the pain killers are present in 1–50% by weight, and preferably are present on the order of about 10–20%, optimally about 15%.

Another important class of compounds present in the cream of this invention is a promotor of subcutaneous absorption such as lecithin (phosphatidylcholine), Vitamin E, menthol, eucalyptol, d-limonene, glyceryl, monostearate and the like. These promoters of subcutaneous absorption are present in an effective amount, which is normally 1–50% by weight, are preferably present on the order of about 10–20% and optimally are about 15% by weight.

Another use of this invention is as a sun burn treatment. There are two substantial modifications that are preferred in this situation. Because the patient's skin is involved over a large area, the concentration of active ingredients are preferably lower to avoid additional irritation. Because capillaries are normally over dilated by sun burn, it is preferred to eliminate the vasodilators and, instead, incorporate a vasoconstrictor such as an antihistamine of which BENADRYL is a suitable choice. Capsaicin is normally present in a range of 0.25–2.5% by weight with a preferred amount on the order of about 0.5%, the norepinephrine inhibitor is present in a range of 0.5–5% with a preferred amount on the order of about 1%, the pain killer is present in a range of 3–35% by weight with a preferred amount on the order of about 15% and the BENADRYL present in the range of 0.5–10% by weight and preferably on the order of about 2%.

The following examples are typical of this invention and may differ because they are attempting to treat slightly different conditions:

EXAMPLE 1

A typical treatment of diabetic or necrotic ulceration may contain the following ingredients, by weight:

| | |
|---|---|
| capsaicin | .5% |
| amitriptyline | 31% |
| ibuprophen | 26% |
| reserpine | 31% |
| lecithin | 1.5% |
| cream | 10%. |

EXAMPLE 2

A typical treatment of burns may contain the following ingredients, by weight:

| | |
|---|---|
| capsaicin | 2.5% |
| nortriptyline | 25% |
| aspirin | 42% |
| nitroglycerin | 22% |
| menthol | .5% |
| lotion | 8%. |

EXAMPLE 3

A typical treatment of bursitis, such as from tennis elbow, may contain the following ingredients, by weight:

| | |
|---|---|
| capsaicin | 5% |
| doxepin | 10% |
| fenoprofen | 30% |
| hydralazine | 5% |
| eucalyptol | 41% |
| cream | 9%. |

EXAMPLE 4

A typical treatment for low back pain may contain the following ingredients, by weight:

| | |
|---|---|
| capsaicin | 1% |
| guanidine | 25% |
| hydrocortisone | 20% |
| reserpine | 19% |
| glyceryl monostearate | 15% |
| cream | 20%. |

EXAMPLE 5

A typical treatment for carpal tunnel syndrome may contain the following ingredients, by weight:

| | |
|---|---|
| capsaicin | .5% |
| guanethidine | 29.5% |
| phenylbutazone | 25% |
| nitroglycerin | 25% |
| Vitamin E | 10% |
| cream | 10%. |

EXAMPLE 6

A typical treatment for Raynaud's syndrome or RSDS may contain the following ingredients, by weight:

| | |
|---|---|
| capsaicin | 1% |
| amitriptyline | 14% |
| naproxen | 40% |
| hydralazine | 13% |
| lecithin | 17% |
| lotion | 15%. |

EXAMPLE 7

A typical treatment for neuritis may contain the following ingredients, by weight:

| | |
|---|---|
| capsaicin | 1% |
| doxepin | 14% |
| tolmetin | 37% |
| reserpine | 20% |
| menthol | 22% |
| ointment | 6%. |

EXAMPLE 8

A typical treatment for fibromyalgia may contain the following ingredients, by weight:

| | |
|---|---|
| capsaicin | .5% |
| guanidine | 25.5% |
| ibuprophen | 20% |
| nitroglycerin | 32% |
| Vitamin E | 15% |
| cream | 7%. |

EXAMPLE 9

A typical sun burn preparation may contain the following ingredients, by weight:

| | |
|---|---|
| capsaicin | .5% |
| doxepin | 1% |
| methyl salicylate | 10% |
| ibuprofen | 5% |
| hydrocortisone | 2% |
| lidocaine | 1% |
| Benadryl | 2% |
| Vitamin E oil | 20% |
| cream | 58.5%. |

Case History #1

A 64 year old Caucasian female was seen with a diabetic ulceration, approximately one centimeter in diameter, on the lateral aspect of the left foot. This was treated utilizing a cream made essentially in accordance with Example 1. This cream was applied three times per day. There was significant improvement, within twenty days. After thirty days, the ulceration had completely granulated closed.

Case History #2

A 28 year old Caucasian female was seen with a second degree burn, approximately fifteen millimeters in diameter on the dorsum of the right foot. This was treated utilizing essentially the lotion of Example 2. This lotion was applied four times per day. There was significant improvement within ten days and total healing within twenty days.

Case History #3

A 50 year old Caucasian male was seen with a very sore "tennis elbow" in the right arm. This was treated utilizing a cream made essentially in accordance with Example 3. This cream was applied to the right elbow. Within several minutes, the pain was totally relieved and the patient was able to play tennis pain free. The patient applied the cream each night for the ensuing four nights and remained pain free.

Case History #4

A 28 year old Caucasian female was seen with a moderate to severe sunburn, on her arms and shoulders. This was treated using a cream made in accordance with Example 9. The cream was applied four times per day. There was significant improvement within five minutes and total healing within three days.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. A topical therapeutic preparation for application to a treatment area of a patient's body comprising an effective amount of capsaicin, an effective amount of a norepinephrine inhibitor, and an effective amount of a vasodilator whereby the capsaicin reduces pain in the treatment area and the norepinephrine inhibitor acts to promote blood circulation in the treatment area and the vasodilator dilates small blood vessels in the treatment area.

2. The topical therapeutic preparation of claim 1 wherein the norepinephrine inhibitor is selected from the group consisting of amitriptyline, nortriptyline, doxepin, guanidine, guanethidine and mixtures thereof.

3. The topical therapeutic preparation of claim 2 wherein the capsaicin is 0.01–1% by weight and the norepinephrine inhibitor is 1–50% by weight.

4. The topical therapeutic preparation of claim 1 wherein the vasodilator is selected from the group consisting of reserpine, nitroglycerin, hydralazine and mixtures thereof.

5. The topical therapeutic preparation of claim 2 further comprising a promotor of transcutaneous absorption.

6. The topical therapeutic preparation of claim 5 wherein the promotor of transcutaneous absorption is selected from the group consisting of lecithin, Vitamin E, menthol, eucalyptol, glyceryl monostearate, d-limonene and mixtures thereof.

7. The topical therapeutic preparation of claim 2 further comprising a pain killer.

8. The topical therapeutic preparation of claim 7 wherein the pain killer comprises an anti-inflamminant.

9. The topical therapeutic preparation of claim 8 wherein the anti-inflamminant is selected from the group consisting of aspirin, hydrocortisone and mixtures thereof.

10. The topical therapeutic preparation of claim 9, wherein the pain killer is selected from the group consisting of hydrocortisone cream, non-steroidal anti-inflamminants, lidocaine, benzocaine and mixtures thereof.

11. A topical therapeutic preparation for application to a treatment area of a patient's body comprising an effective amount of capsaicin and an effective amount of a vasodilator selected from the group consisting of reserpine, nitroglycerin, hydralazine and mixtures thereof whereby the capsaicin reduces pain in the treatment area and the vasodilator acts to promote blood circulation in the treatment area.

12. A topical therapeutic preparation comprising
an effective amount of capsaicin;
a norepinephrine inhibitor selected from the group consisting of amitriptyline, nortriptyline, doxepin, guanidine, guanethidine and mixtures thereof whereby the capsaicin cream reduces pain in a treatment area and the norepinephrine inhibitor acts to promote blood circulation in the treatment area;

a vasodilator acting to promote blood circulation in the treatment area and being selected from the group consisting of reserpine, nitroglycerin, hydralazine and mixtures thereof;

a promotor of transcutaneous absorption selected from the group consisting of lecithin, Vitamin E, menthol, eucalyptol, glyceryl monostearate, d-limonene and mixtures thereof;

a pain killer selected from the group consisting of hydrocortisone, non-steroidal anti-inflamminants, lidocaine, benzocaine and mixtures thereof; and a therapeutically acceptable carrier.

13. A method of treating pain and promoting healing comprising tropically applying, in a treatment area, to a patient having superficial pain, an effective amount of a composition comprising a therapeutically acceptable carrier, capsaicin, and a norepinephrine inhibitor, the capsaicin being present from about 0.01% to about 1.0% by weight and the norepinephrine inhibitor being present from about 1–50% by weight whereby the capsaicin reduces pain in the treatment area and the norepinephrine inhibitor acts to promote blood circulation in the treatment area.

14. The method of claim 13 wherein the composition comprises an effective amount of a vasodilator.

15. The method of claim 13 wherein the vasodilator is selected from the group consisting of reserpine, nitroglycerin, hydralazine and mixtures thereof.

16. The method of claim 13 wherein the norepinephrine inhibitor is selected from the group consisting of amitriptyline, nortriptyline, doxepin, guanidine, guanethidine and mixtures thereof.

17. The method of claim 13 wherein the composition comprises a promotor of transcutaneous absorption selected from the group consisting of lecithin, Vitamin E, menthol, eucalyptol, glyceryl monostearate, d-limonene and mixtures thereof.

18. The method of claim 13 wherein the composition comprises an anti-inflamminant selected from the group consisting of aspirin, hydrocortisone and mixtures thereof.

19. The method of claim 13 wherein the composition comprises a pain killer is selected from the group consisting of hydrocortisone cream, non-steroidal anti-inflamminants, lidocaine, benzocaine and mixtures thereof.

* * * * *